United States Patent [19]

Suzuki et al.

[11] 4,306,958
[45] Dec. 22, 1981

[54] COLORING-DECOLORING-DRYING APPARATUS FOR ELECTROPHORESIS

[75] Inventors: Hideo Suzuki, Tokyo; Hideaki Ida, Musashimurayama, both of Japan

[73] Assignee: Olympus Optical Co., Ltd., Tokyo, Japan

[21] Appl. No.: 206,176

[22] Filed: Nov. 12, 1980

[30] Foreign Application Priority Data

Nov. 13, 1979 [JP] Japan ................. 54-146837

[51] Int. Cl.$^3$ ............................ G01N 27/26
[52] U.S. Cl. .................... 204/300 R; 204/180 G; 204/180 S; 204/180 R; 204/299 R
[58] Field of Search .......... 204/180 G, 180 S, 180 R, 204/299 R, 300 R, 300 EC, 181 F

[56] References Cited

U.S. PATENT DOCUMENTS

| 2,820,752 | 1/1958 | Heller | 204/300 EC X |
| 3,020,224 | 2/1962 | Blank et al. | 204/300 EC X |
| 3,502,563 | 3/1970 | Schmidt | 204/300 EC X |
| 3,835,005 | 9/1974 | Dudley et al. | 204/300 EC X |
| 3,930,880 | 1/1976 | Hoefer | 204/180 G X |
| 4,021,324 | 5/1977 | Delony et al. | 204/180 R X |
| 4,084,541 | 4/1978 | Ito | 204/180 R X |
| 4,115,234 | 9/1978 | Anselrode | 204/180 R X |

Primary Examiner—Arthur C. Prescott
Attorney, Agent, or Firm—Cushman, Darby & Cushman

[57] ABSTRACT

A coloring-decoloring-drying apparatus for electrophoresis comprising a coloring-decoloring container having an opening used for insertion of the carrier and pouring coloring and decoloring liquid agents, rollers arranged in the vicinity of the opening of said coloring-decoloring container, and an inverted U-shaped drain pipe having one port located inside said container and in the vicinity of the bottom thereof and the other port located outside said container at a height lower than the bottom of said container, and adapted in such a manner that a carrier having been subjected to electrophoresis in an electrophoretic apparatus is fed into said coloring-decoloring container by operating said rollers, the tailing end of the carrier is held between said rollers, a coloring liquid agent is poured into said container through said opening for coloring said carrier while it is held in the condition described above, said coloring liquid agent is discharged through said drain pipe after said carrier has been colored, a decoloring liquid agent is poured for decoloring said carrier, said decoloring liquid agent is discharged after said carrier has been decolored, and then the carrier is dried by blowing hot air blast. Said coloring-decoloring-drying apparatus for electrophoresis is so designed as to be capable of performing coloring, decoloring and drying of a carrier without injuring or tearing the carrier and eliminate the necessity to arrange a valve for discharging the liquid agents.

5 Claims, 9 Drawing Figures

COLORING-DECOLORING-DRYING APPARATUS FOR ELECTROPHORESIS

BACKGROUND OF THE INVENTION (a) Field of the Invention

The present invention relates to an apparatus for coloring, decoloring and drying sample carriers in electrophorestic systems.

(b) Description of the Prior Art

The electrophoresis is utilized for measuring proteins contained in blood serum in clinical inspection laboratories, etc. of hospitals and medical institutes. For the electrophoresis, blood serum to be analyzed is applied onto a carrier which is made of cellurose acetate or the similar material and then the carrier is electrically energized for developing fractionated patterns of the blood serum. The carrier is colored with a coloring liquid agent and, after the area other than the blood serum is decolored, the sample is subjected to colorimetry for quantitative determination. Conventionally, various processes of the electrophoresis were manually carried out with low efficiency. Further, analysis by the electrophoresis required highly delicate skill and the conventional electrophoretic system had a defect that it offered analytical results which are different depending on individual analysts' measuring skills.

In view of such circumstances, there have hitherto been developed automatic electrophoretic systems which can automatically carry out the processes of the electrophoresis for the purpose of enhancing measuring efficiency and eliminating analytical variations due to difference in measuring skills depending on indivisual analysts. As an apparatus for carrying out the coloring, decoloring and drying processes out of the various steps performed by the automatic electrophoretic systems, there has known an apparatus disclosed by Japanese published unexamined patent application No. 158694/54 (U.S. Pat. No. 4,222,843). This coloring-decoloring-drying apparatus is designed in such a manner that a carrier is bonded onto circumference of a drum, rotated therewith so as to pass through a liquid trough filled with a coloring liquid agent for coloring said carrier and then through a trough filled with a decoloring liquid agent for decoloring said carrier, and then is dried by exposing it to hot air blast or the similar means. An outline of this coloring-decoloring-drying apparatus will be described with reference to FIG. 1. A carrier 1 on which fractionated patterns of a sample have been developed in an electrophoretic apparatus (not shown) is fed between a roller 2 and a drum 3 by an adequate means. The carrier is soaked with a buffer solution and is therefore bonded onto the drum 3 consecutively from the leading end of said carrier. When the leading end of the carrier has passed just beyond another roller 4, rotation of the drum is stopped so that the carrier 1 is kept in the condition where it is bonded onto the outer circumference of the drum 3 while being held with both the rollers 2 and 4. With the carrier 1 kept in this condition, the drum 3 is rotated together with the rollers 2 and 4 so as to rotate the carrier 1 while it is bonded onto the drum 3 and held with the rollers 2 and 4. A liquid trough 5 is filled with a coloring liquid agent, and therefore the carrier is colored since it passes through the liquid agent repeatedly during its rotation. The carrier is decolored in the similar way when the trough is filled with a decoloring liquid agent in place of the coloring liquid agent. After the carrier has been colored and decolored as described above, it is dried with hot air blast supplied from a blower port (now shown), and then the drum 3 only is rotated to feed the carrier 1 to the next process.

The coloring-decoloring-drying apparatus described above has a surface 3a having a curvature lower than the imaginary circular circumference of the drum 3 and serving to prevent the carrier 1 from being torn due to contraction at the drying process. Since degree of the contraction is different depending on material of the carrier, curvature of the surface 3a should ideally be varied depending on contraction degree of the carrier. Further, when the carrier has a short length, it is required to use a drum having a small diameter. In such a case, the carrier bonded onto the drum is held in a strongly curved condition and such a curved form remains at the subsequent processes, thereby causing inconvenience at the processes after the coloring and decoloring. Moreover, the drum type of apparatus shown in FIG. 1 has a drawback that it has a very complicated mechanism and requires a large number of component parts.

SUMMARY OF THE INVENTION

A general object of the present invention is to provide a coloring-decoloring-drying apparatus for electrophoresis comprising a coloring-decoloring container having an opening for inserting and sending out the carrier, rollers arranged in the vicinity of the opening of said coloring-decoloring container and an inverted U-shaped drain tube having one port located in the vicinity of the bottom of said coloring-decoloring container and the other port located outside said container at a height lower than the bottom thereof, said apparatus being adapted in such manner that the carrier is fed by said rollers into said coloring-decoloring container, then suspended in said container in a condition where the tailing end of the carrier is held between said rollers, colored and decolored by pouring coloring and decoloring liquid agents into said container and then dried by blowing hot air blast into said container.

DETAILED DESCRIPTION OF THE PREFERRED EMBODIMENT

Now, the present invention will be described more detailedly with reference to the preferred embodiment illustrated in the accompanying drawings.

Figure 1:
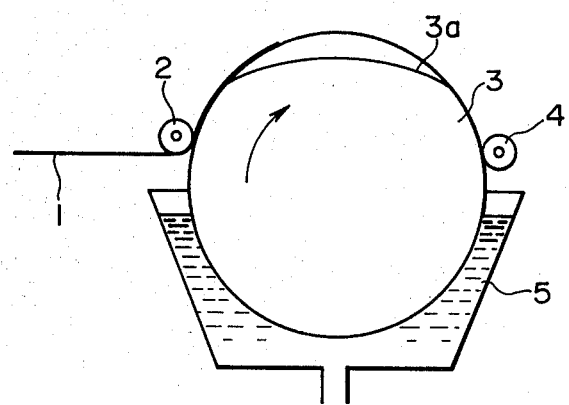
FIG. 1 shows a sectional view schematically illustration outline of the conventional coloring-decoloring-drying apparatus.
Figure 2:
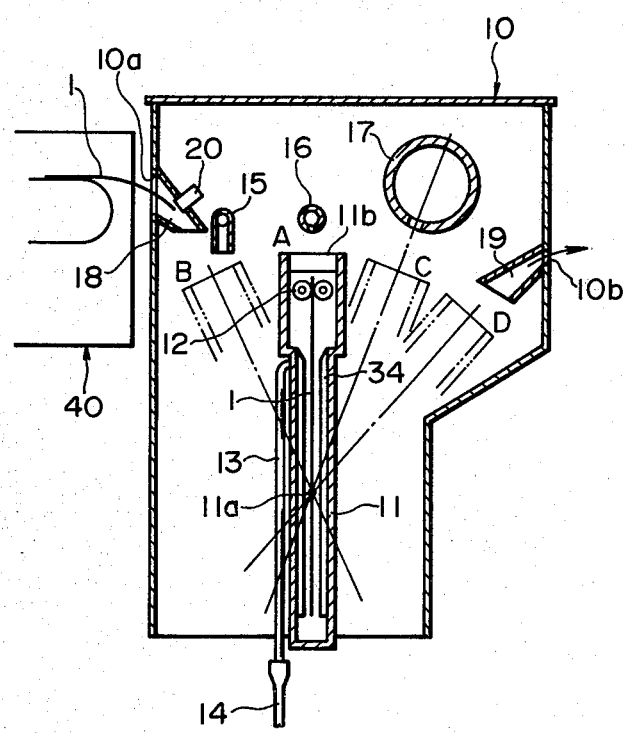
FIG. 2 shows a sectional view illustrating construction of the coloring-decoloring-drying apparatus according to the present invention.
Figure 3:
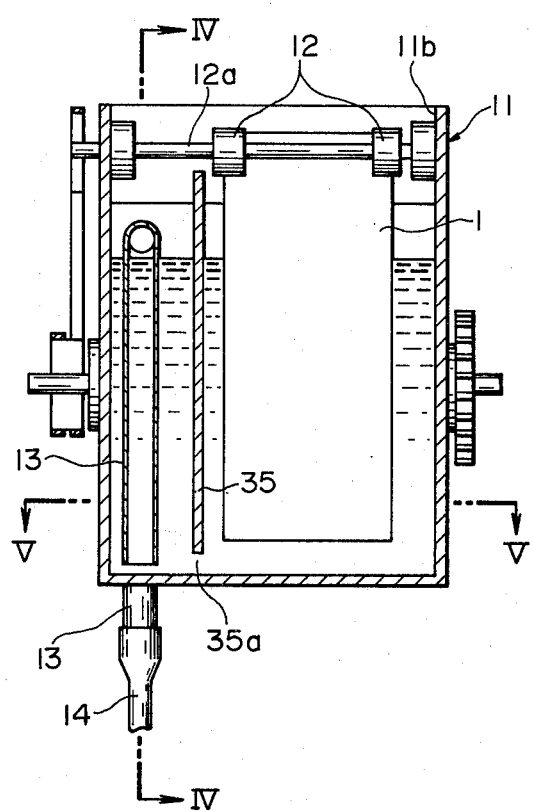
FIG. 3 shows a sectional view illustrating construction of the coloring-decoloring container to be used in the coloring-decoloring-drying apparatus according to the present invention.
Figure 4:
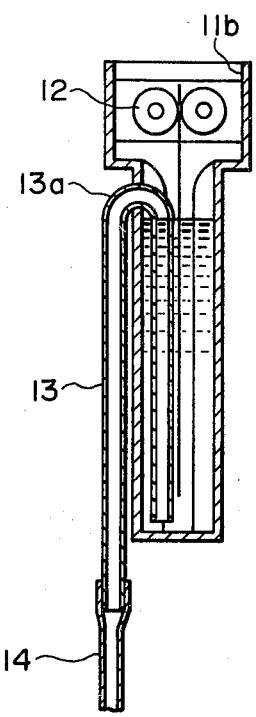
FIG. 4 shows a sectional view taken along the IV—IV line of FIG. 3.

In FIG. 2, the reference numeral 10 represents a main casing of the coloring-decoloring-drying apparatus according to the present invention, and the reference numeral 11 designates a coloring-decoloring container which is rotatably arranged around an axis 11a in the main casing 10 and has such a construction as shown on larger scales in FIG. 3 and FIG. 4. The reference numeral 12 denotes rollers which are arranged in the vicinity of opening 11a of the coloring-decoloring container 11 and one of which is rotated with rotation of a shaft 12a for feeding the carrier 1 into the container 11, both the rollers serving thereafter for holding the carrier 1 as shown in FIG. 3 and FIG. 4. The reference numeral 13 represents a drain pipe which is arranged in the vicinity of one end of the container 11 and has an inverted U-shape having a portion located inside the coloring-decoloring container 11 and the other portion located outside said container. One port of this drain pipe 13 (at the end arranged inside the container 11) is located near the bottom of the container 11 and the other port (at the end arranged outside the container 11) is located lower than the bottom of the container 11. The reference numeral 14 designates a drain tube connected to one end of the drain pipe 13. The reference numeral 15 denotes a coloring liquid agent nozzle, the reference numeral 16 represents a decoloring liquid agent nozzle, the reference numeral 17 designates a drying air pipe, the reference numerals 18 and 19 denote guides and the reference numeral 20 represents a carrier detector such as a photo sensor.

Now, operations of the coloring-decoloring-drying apparatus having the above-described construction will be described. In the first place, the coloring-decoloring container 11 is turned counterclockwise around the axis 11a from the position shown in the solid lines (indicated by the reference symbol A) to the position indicated by the reference symbol B. In this condition, the carrier 1 which has been subjected to electrophoresis in an electrophoretic apparatus 40 is sent out of the electrophoretic apparatus 40 and fed into the main casing 10. The carrier is directed by the guide 18 toward the coloring-decoloring container kept at the position B. Upon detection of feeding of the carrier 1 with a carrier detector 20, the roller 12 starts rotating for sending the carrier 1 deep into the container 11. When the rear end of the carrier 1 reaches the vicinity of the rollers 12, these rollers are stopped so that the carrier is kept in suspended condition in the coloring-decoloring container 11 with one end of said carrier held between both the rollers. At this stage, a coloring liquid agent is poured through the coloring liquid agent nozzle 15 into the container 11 until the liquid level reaches a little lower than the top end, i.e., bending 13a of the drain pipe arranged inside the container 11. Therefore, the carrier is kept in the container 11 while being dipped in the coloring liquid agent. These operations may be performed in the reverse sequence. That is to say, the carrier 1 may be sent into the container 11 after it is filled with the coloring liquid agent. The carrier 1 is kept in the container 11 for a definite time as it is depped in the coloring liquid agent. After the carrier 1 has been colored sufficiently, the coloring liquid agent is poured again through the coloring liquid agent nozzle 15 until the liquid level becomes higher than the bending 13a of the drain pipe 13. In this condition, the coloring liquid agent is drained under the siphon effect through the drain pipe 13 and drain tube 14.

In the next place, the coloring-decoloring container 11 is returned to the position A and a decoloring liquid agent is poured into the container 11 until the liquid level reaches a little lower than the bending 13a of the drain pipe 13 in the container 11 for decoloring the carrier 1. After a definite time elapsed, the decoloring liquid agent is added, whereby the decoloring liquid agent is drained from the container 11 under the siphon effect through the drain pipe 13 and tube 14. This decoloring process is repeated until the carrier 1 is decolored completely.

After completion of the decoloring process, the coloring-decoloring container 11 is turned clockwise and stopped at the drying position (indicated by the reference symbol C) at which the upper opening 11a thereof is located under the drying air pipe 17. With the coloring-decoloring container 11 kept in this position, hot air blast is supplied from the drying air pipe 17 for drying the carrier 1. After the carrier has been dried completely, the coloring-decoloring container 11 is turned further clockwise until it reaches the carrier sending out position (indicated by the reference symbol D). With the container 11 kept in this position, rollers 12 are rotated to send out the carrier 1 through guide 19 and sending out port 10b to the next process.

Figure 5:
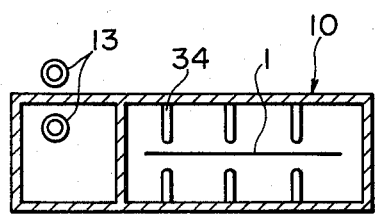
FIG. 5 shows a sectional view taken along the V—V line of FIG. 3.
Figure 6:
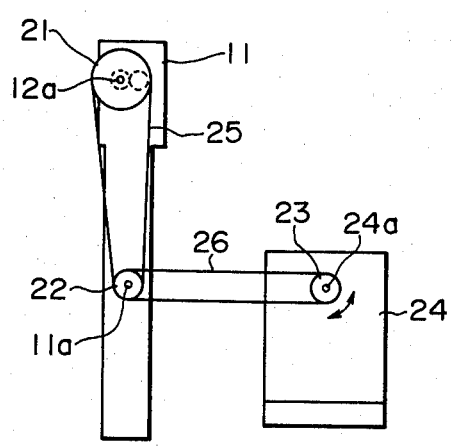
FIG. 6 shows a side view illustrating a mechanism for rotating the rollers in the coloring-decoloring-drying apparatus according to the present invention.
Figure 7:
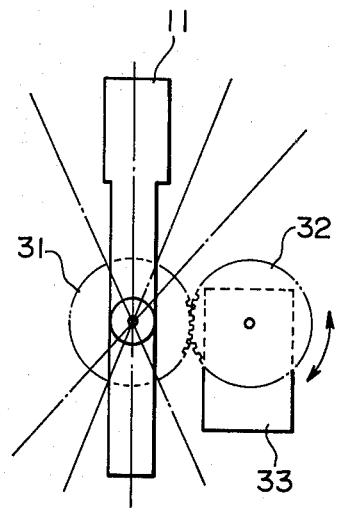
FIG. 7 shows a plan view illustrating a mechanism for turning the coloring-decoloring container in the coloring-decoloring-drying apparatus according to the present invention.
Figure 8:
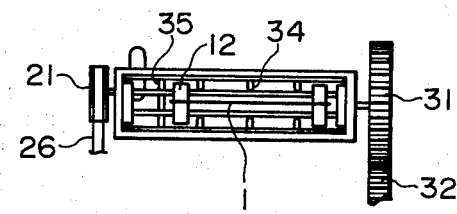
FIG. 8 shows a plan view illustrating construction of said coloring-decoloring container.

Now, the mechanism for turning the coloring-decoloring container and rotating the rollers of the coloring-decoloring-drying apparatus will be described. FIG. 6 shows a side view illustrating construction of the mechanism for driving the rollers 12 arranged in the coloring-decoloring container 11. The reference numeral 21 represents a pulley fixed to the shaft 12a of one of the rollers 12, the reference numeral 22 designates a second pulley attached to the turning shaft 11a of the coloring-decoloring container 11, the reference numeral 23 denotes a third pulley attached to a rotating shaft 24a of a motor 24 for driving the rollers, and the reference numerals 25 and 26 represent belts which are passed around a pair of pulleys 21 and 22 and another pair of pulleys 22 and 23 respectively. When the motor 24 is rotated in either direction in this mechanism, the carrier 1 is fed or sent into or out of the container 11 by operating the pulleys 22, 23, etc. as well as the belts 25 and 26. FIG. 7 shows a side view illustrating construction of the mechanism for turning the coloring-decoloring container 11. In FIG. 7, the reference numeral 31 represents a gear fixed to the turning shaft 11a (on the surface located on the opposite side of the pulley 22 shown in FIG. 6) of the coloring-decoloring container 11, the reference numeral 32 designates another gear which is in mech with the gear 31, and the reference numeral 33 denotes a motor for turning the coloring-decoloring container. When the motor is rotated in either direction in this mechanism, the coloring-decoloring container 11 is turned clockwise or counterclockwise. Though the mechanism for rotating the rollers and the mechanism for turning the coloring-decoloring container are illustrated separately in FIG. 6 and FIG. 7 respectively, these mechanisms are actually arranged on both the right and left sides of the coloring-decoloring container as shown in FIG. 8. In addition, the member represented by the reference numeral 34 in FIG. 2, FIG. 5, etc, is fins which serve for preventing the carrier 1 from adhering to the inside wall of the container 11. In addition, the reference numeral 35 used in FIG. 3 through FIG. 5 designates a partition plate which separates the in flow side from out flow side of hot air blast for drying the carrier 1. In other words, the hot air blast supplied from drying air pipe 17 into the coloring-decoloring container 11 flows downward along the carrier 1, passes through the opening 35a formed in the lower end of the partition plate 35, circulates to the left side in FIG. 3 and then flows out upward.

Figure 9:
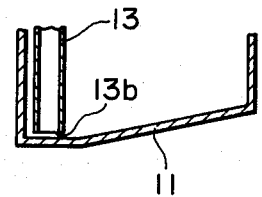
FIG. 9 shows a sectional view illustrating another example of the coloring-decoloring container to be used in the coloring-decoloring-drying apparatus according to the present invention.

FIG. 9 shows a variant example of the coloring-decoloring container 11 having a slanted bottom surface and comprising the port 13b of the drain pipe 13 located on the lower side. This type of the coloring-decoloring container makes it possible to reduce quantity of liquid agent remaining after draining.

As is understood from the foregoing descriptions, the coloring-decoloring-drying apparatus according to the present invention permits coloring and decoloring the carrier while keeping it in suspended condition with one end thereof held between the rollers, and is free from the defect of forming curved shape of the carrier, or injuring or tearing the carrier due to contraction in the drying process. Since said coloring-decoloring-drying apparatus utilizes the siphon effect, it eliminates the necessity to arrange a valve in the liquid draining path. Further, the coloring-decoloring-drying apparatus according to the present invention has a simple construction consisting only of the coloring-decoloring container, the rollers arranged therein and so on.

Moreover, drying effect can be enhanced by arranging a partition plate inside the coloring-decoloring container.

We claim:
1. A carrier coloring-decoloring-drying apparatus for electrophoresis comprising a coloring-decoloring container having an opening used for insertion of the carrier and pouring coloring and decoloring liquid agents, rollers arranged inside said coloring-decoloring container and used for inserting and sending out said carrier, and an inverted U-shaped drain pipe having one port located inside said container and in the vicinity of the bottom of said coloring-decoloring container and the other port located outside said container at a height lower than the bottom of said container, said apparatus being adapted in such a manner that the carrier having been subjected to electrophoresis is fed into said coloring-decoloring container by rotating said rollers, said carrier is kept in suspended condition with its tailing end held between said rollers, a coloring liquid agent is poured through said opening to color said carrier, then said coloring liquid agent is discharged through said drain pipe after said carrier has been colored, a decoloring liquid agent is poured through said opening to decolor said carrier, then said decoloring liquid agent is discharged through said drain pipe after said carrier has been decolored, and then said carrier is dried by blowing hot air blast through said opening.

2. A carrier coloring-decoloring-drying apparatus for electrophoresis according to claim 1 wherein the area near said drain pipe is made lower than the other areas on the bottom of said coloring-decoloring container.

3. A carrier coloring-decoloring-drying apparatus for electrophoresis according to claim 2 wherein the bottom of said coloring-decoloring container is slanted and the lowest area of the bottom is arranged in the vicinity of the port of said drain pipe.

4. A carrier coloring-decoloring-drying apparatus for electrophoresis according to claim 1 wherein a partition plate having an opening near the bottom thereof is arranged inside said coloring-decoloring container.

5. A carrier coloring-decoloring-drying apparatus for electrophoresis according to claim 4 wherein said partition plate is arranged between the position of said carrier when it is held in said container and the position of said drain pipe.

* * * * *